United States Patent
Birnberg et al.

(10) Patent No.: US 8,273,744 B2
(45) Date of Patent: Sep. 25, 2012

(54) AMPK MODULATORS

(75) Inventors: Neal C. Birnberg, Lexington, MA (US); Hong Liu, Wilmington, MA (US); Qing Ping Weng, Wellesley, MA (US); Haibo Shang, North Reading, MA (US); Pan Yin, Billerica, MA (US); Sharanappa B. Rajur, Andover, MA (US); Hwa-Ok Kim, Lexington, MA (US); Paresh D. Salgaonkar, Malden, MA (US); Norton P. Peet, North Andover, MA (US)

(73) Assignee: Mercury Therapeutics, Inc., Woburn, MA (US)

( * ) Notice: Subject to any disclaimer, the term of this patent is extended or adjusted under 35 U.S.C. 154(b) by 0 days.

(21) Appl. No.: 12/365,671

(22) Filed: Feb. 4, 2009

(65) Prior Publication Data

US 2010/0009992 A1  Jan. 14, 2010

Related U.S. Application Data

(60) Provisional application No. 61/026,001, filed on Feb. 4, 2008, provisional application No. 61/051,200, filed on May 7, 2008.

(51) Int. Cl.
| | |
|---|---|
| A01N 43/58 | (2006.01) |
| A01N 43/42 | (2006.01) |
| A01N 43/38 | (2006.01) |
| A61K 43/60 | (2006.01) |
| A61K 31/44 | (2006.01) |
| A61K 31/405 | (2006.01) |
| C07D 471/00 | (2006.01) |
| C07D 215/00 | (2006.01) |
| C07D 209/04 | (2006.01) |

(52) U.S. Cl. ........ 514/249; 514/300; 514/312; 514/415; 544/350; 546/155; 548/469

(58) Field of Classification Search ........................ None
See application file for complete search history.

(56) References Cited

U.S. PATENT DOCUMENTS

| | | | |
|---|---|---|---|
| 6,265,403 | B1 | 7/2001 | Fraley et al. |
| 6,369,072 | B2 | 4/2002 | Malamas et al. |
| 7,119,205 | B2 | 10/2006 | Iyengar et al. |
| 2003/0203959 | A1* | 10/2003 | Rauer et al. ............... 514/414 |
| 2004/0209897 | A1 | 10/2004 | Vernier et al. |
| 2005/0004114 | A1 | 1/2005 | Whitehouse et al. |
| 2006/0287356 | A1 | 12/2006 | Iyengar et al. |
| 2007/0191371 | A1 | 8/2007 | Bennett et al. |

FOREIGN PATENT DOCUMENTS

| | | |
|---|---|---|
| AU | 729320 | 2/2001 |
| EP | 1 780 202 A1 | 5/2007 |
| JP | 2000204091 A | 7/2000 |
| WO | 200224694 A1 | 3/2002 |
| WO | 03/030909 A1 | 4/2003 |
| WO | 2006048620 A2 | 5/2006 |
| WO | 2006055725 A2 | 5/2006 |
| WO | 2006080821 A1 | 8/2006 |
| WO | 2007/019397 A2 | 2/2007 |
| WO | 2007084667 A2 | 7/2007 |
| WO | 2007/088978 A1 | 8/2007 |
| WO | 2008007900 A1 | 1/2008 |
| WO | 2008012326 A1 | 1/2008 |

OTHER PUBLICATIONS

Schaefer et al. Failure is not an option: learning from unsuccessful proof-of-concept trials. Drug Discovery Today, 2008, 13(21/22), pp. 913-916.*
Horig et al. Review: From bench to clinic and back: Perspective on the 1$^{st}$ IQPC Translational Research Conference. Journal of Translational Medicine, 2004, 2(44).*
Burgers Medicinal Chemistry and Drug Discovery, Fifth Edition, vol. I: Principles and Practice, Wiley-Interscience, 1995, pp. 783-802.*
Foye's Principles of Medicinal Chemistry, Willaims et al. 5$^{th}$ Edition, 2002), title page and pp. 58-69.*
International Search Report for PCT/US09/33077 dated Mar. 31, 2009.
Shim, et al., Bioorg. & Med Chem. Letters, "Formylchromone Derivatives as a Novel Class of Protein Tyrosine Phosphatase 1B Inhibitors", 13:2561-2563, 2003.

* cited by examiner

*Primary Examiner* — Brandon Fetterolf
*Assistant Examiner* — Anna Pagonakis
(74) *Attorney, Agent, or Firm* — Elmore Patent Law Group, P.C.; Edgar W. Harlan; Carolyn S. Elmore

(57) ABSTRACT

The present invention relates to compounds and pharmaceutically acceptable salts, esters and prodrugs of Formula (I) or (II):

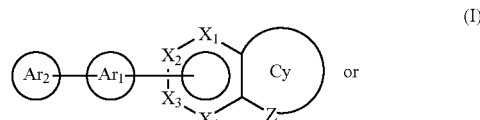

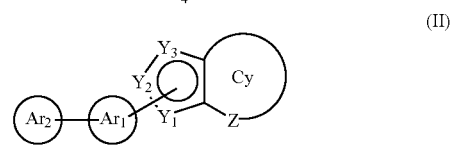

which are useful as AMPK modulators effective in treating diabetes, obesity and cancer in a subject.

12 Claims, No Drawings

AMPK MODULATORS

RELATED PARAGRAPH

This application claims the benefit of U.S. Provisional Application No. 61/026,001, filed on Feb. 4, 2008 and U.S. Provisional Application No. 61/051,200, filed on May 7, 2008, the contents of which are herein incorporated by reference.

BACKGROUND OF THE INVENTION

The AMP-activated protein kinase (AMPK) acts as an intracellular metabolic sensor in a variety of cells, where it monitors and responds to variations in the AMP:ATP ratio (Hardie et al., *Annu. Rev. Biochem.* 67:821-855, 1998). Upon activation of AMPK, the enzyme phosphorylates a number of protein substrates to decrease further ATP usage by the cell. AMPK is a heterotrimeric complex consisting of a catalytic subunit ($\alpha$) and two associated subunits ($\beta$ and $\gamma$). Both the $\beta$ and $\gamma$ subunits are required for optimal activity of the $\alpha$ catalytic subunit. The AMPK complex is evolutionarily conserved and also can be found in yeast and plants. Mammalian AMPK is composed of different isoforms of subunits: $\alpha 1$, $\alpha 2$, $\beta 1$, $\beta 2$, $\gamma 1$, $\gamma 2$, and $\gamma 3$ Hardie and Hawley, *BioEssays* 23:1112 1119, 2001). Different combinations of isoform subunits are activated differently in vivo, and most likely also differ in substrate utilization. AMPK activity is found in all tissues, including liver, kidney, muscle, lung, and brain (Cheung et al., *Biochem. J.* 346:659-669, 2000).

AMPK is recognized as a major regulator of lipid biosynthetic pathways due to its role in the phosphorylation and inactivation of key enzymes such as acetyl-CoA carboxylase, fatty acid synthase (Hardie and Carling, *Eur. J. Biochem.* 246:259 273, 1997). More recent work has suggested that AMPK has a wider role in metabolic regulation (Winder and Hardie, *Am. J. Physiol.* 277:E1 10, 1999); this includes fatty acid oxidation, muscle glucose uptake, expression of cAMP-stimulated gluconeogenic genes such as PEPCK and G6Pase, and expression of glucose-stimulated genes associated with hepatic lipogenesis, including fatty acid synthase, Spot-14, and L-type pyruvate kinase. Chronic activation of AMPK also can induce the expression of muscle hexokinase and glucose transporters (Glut4), mimicking the effects of extensive exercise training (Holmes et al. *J. Appl. Physiol.* 87:1990 1995, 1999).

AMPK phosphorylates and modifies the activity of key enzymes of carbohydrate metabolism. In fact, AMPK plays an important part in lipogenesis, because it inhibits the synthesis of fatty acids and of cholesterol by inactivating acetyl-CoA carboxylase and HMG coreductase. AMPK reduces the expression of fatty acid synthase (FAS), which controls the synthesis of triglycerides. In addition, AMPK also reduces the expression of one of the key enzymes of gluconeogenesis (PEPCK), which manifests itself in inhibition of the hepatic production of glucose. AMPK increases the clearance of blood glucose by facilitating the transport of glucose to the skeletal muscle.

All those properties combine to make AMPK a target of choice in the treatment of diabetes and of the metabolic disorders associated therewith, the search for pharmacological activators of AMPK accordingly being of fundamental value to the treatment of those pathologies ((Winder and Hardie, *Am. J. Physiol.* 277:E1 10, 1999).

Compounds such as 5-aminoimidazole-4-carboxamide-1 ($\beta$)-D-ribofuranoside (AICAR) and metformin, have been shown to activate AMPK in vivo at high concentrations (Bergeron, R. et. al. Effect of 5-aminoimidazole-4-carboxamide-1($\beta$)-D-ribofuranoside infusion on in vivo glucose metabolism in lean and obese Zucker rats. *Diabetes* 50:1076 (2001); Song, S. M. et. al. 5-Aminoimidazole-4-darboxamide ribonucleoside treatment improves glucose homeostasis in insulin-resistant diabeted (ob/ob) mice. *Diabetologia* 45:56 (2002); Halseth, A. E. et. al. Acute and chronic treatment of ob/ob and db/db mice with AICAR decreases blood glucose concentrations. *Biochem. and Biophys. Res. Comm.* 294:798 (2002), Buhl, E. S. et. al. Long-term AICAR administration reduces metabolic disturbances and lowers blood pressure in rats displaying feature of the insulin resistance syndrome. *Diabetes* 51: 2199 (2002)). Metformin increases AMP-activated protein kinase activity in skeletal muscle of subjects with type 2 diabetes. *Diabetes,* 51: 2074 (2002)), although it has to be determined to what extent its antidiabetic action relies on this activation. As with leptin and adiponectin, the stimulatory effect of metformin is indirect via activation of an upstream kinase (Zhou, G. et. al. Role of AMP-activated protein kinase in mechanism of metformin action. The *J. of Clin. Invest.,* 108: 1167 (2001)).

Not withstanding recent advances, the need still exists for more effective AMPK modulators.

SUMMARY OF THE INVENTION

Accordingly, the present invention provides a compound having a general formula I or II:

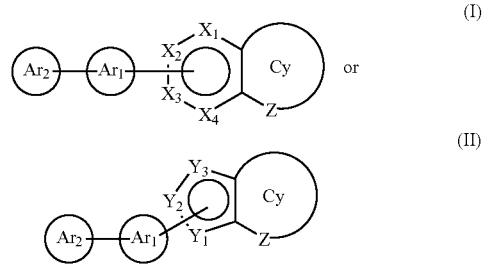

or its geometric isomers, enantiomers, diastereomers, racemates, pharmaceutically acceptable salts, prodrugs and solvates thereof, wherein $X_1$-$X_4$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic;

$Y_1$ is O, N or NH;

$Y_2$-$Y_3$ are independently selected from the group consisting of C, $CR_1$, O, S, N or NH;

is independently selected from the group consisting of heteroaryl, substituted heteroaryl, heterocyclic, substituted heterocyclic; where Z is O, N or NH; and

and

are independently selected from the group consisting of aryl, substituted aryl, heteroaryl, substituted heteroaryl, heterocyclic, substituted heterocyclic, cycloalkyl, substituted cycloalkyl, cycloalkenyl and substituted cycloalkenyl.

It is noted that the compounds throughout refer to geometric isomers, enantiomers, diastereomers, racemates, pharmaceutically acceptable salts, and solvates of the compounds. It is understood that the formulae contain chiral centers and that, where a chiral center is not drawn to define the isomer, active isomers and racemates are intended. Likewise, salts and solvates are defined herein to "comprise" the compound itself.

DETAILED DESCRIPTION OF THE INVENTION

In a first embodiment of the compounds of the present invention are compounds represented by formula (I) or (II) as illustrated above, or its geometric isomers, enantiomers, diastereomers, racemates, pharmaceutically acceptable salts, prodrugs and solvates thereof.

In one embodiment of the compounds of the present invention are compounds represented by formula (III) as illustrated below, or its geometric isomers, enantiomers, diastereomers, racemates, pharmaceutically acceptable salts, prodrugs and solvates thereof:

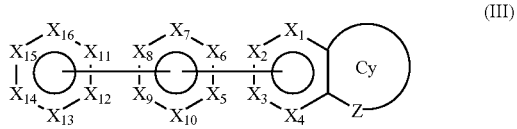

(III)

wherein $X_5$-$X_{16}$ are independently selected from the group consisting of C, $CR_1$ or N, where $R_1$ is $R_1$ is hydrogen or an electron releasing group, such as an electron withdrawing group and is preferably independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; and

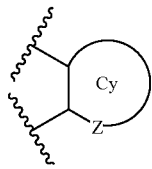

is selected from the group consisting of

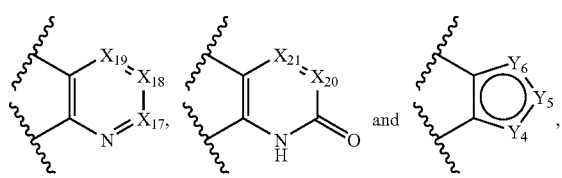

where $X_{17}$-$X_{21}$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; $Y_4$ is O, N or NH; $Y_5$-$Y_6$ are independently selected from the group consisting of C, $CR_1$, O, S, N or NH; and $X_1$-$X_4$ are as defined in the first embodiment.

$R_1$ can also be selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, CHNOH, $CONH_2$, CHO, substituted or unsubstituted alkylsulfonyl, acyl, aliphatic, substituted aliphatic, aryl, heteroaryl, and heterocyclic. The compounds are preferably biaryl substituted indoles, such as

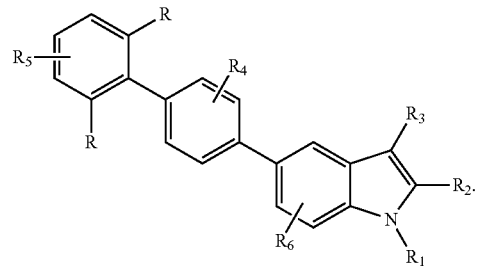

and salts thereof, wherein $R_1$, $R_2$, $R_3$, $R_4$, $R_5$ and $R_6$ are independently hydrogen or one or more electron releasing groups, and each R is selected from H or hydroxyl, wherein at least one R is hydroxyl. The center aryl group can be phenyl or it can be substituted with a pyridine or pyridazine, e.g.:

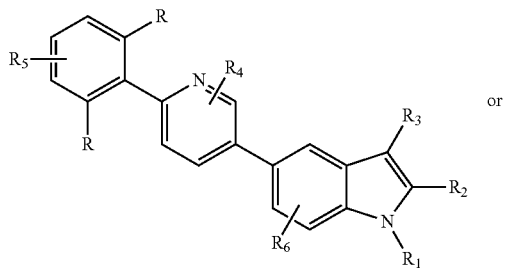

or

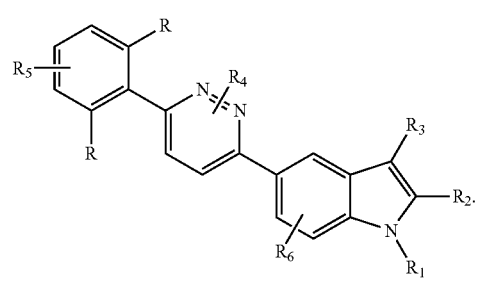

In one embodiment of the compounds of the present invention are compounds represented by formula (IV) as illustrated below, or its geometric isomers, enantiomers, diastereomers, racemates, pharmaceutically acceptable salts, prodrugs and solvates thereof:

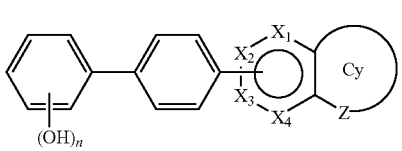

(IV)

wherein

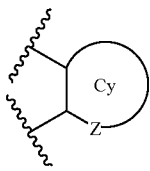

is selected from the group consisting of

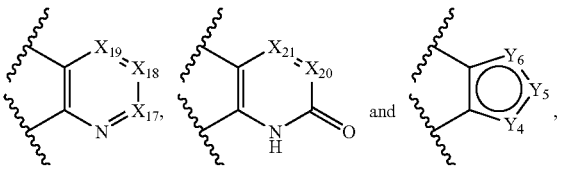

where $X_{17}$-$X_{21}$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; $Y_4$ is O, N or NH; $Y_5$-$Y_6$ are independently selected from the group consisting of C, $CR_1$, O, S, N or NH; n is 1-3, preferably 1 or 2 and $X_1$-$X_4$ are as defined in the first embodiment.

In one embodiment of the compounds of the present invention are compounds represented by formula (V) as illustrated below, or its geometric isomers, enantiomers, diastereomers, racemates, pharmaceutically acceptable salts, prodrugs and solvates thereof:

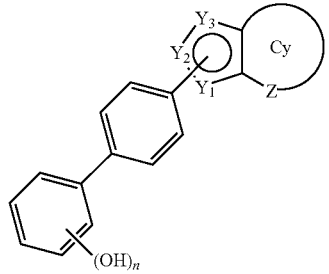

(V)

wherein $X_5$-$X_{16}$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; and

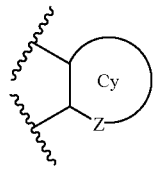

is selected from the group consisting of

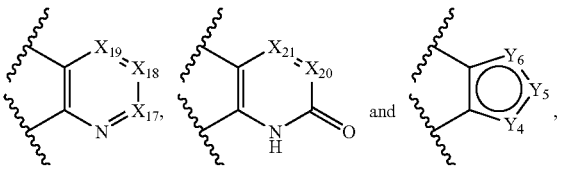

where $X_{17}$-$X_{21}$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; $Y_4$ is O, N or NH; $Y_5$-$Y_6$ are independently selected from the group consisting of C, $CR_1$, O, S, N or NH; and $Y_1$-$Y_3$ are as defined in the first embodiment.

In one embodiment of the compounds of the present invention are compounds represented by formula (VI) as illustrated below, or its geometric isomers, enantiomers, diastereomers, racemates, pharmaceutically acceptable salts, prodrugs and solvates thereof:

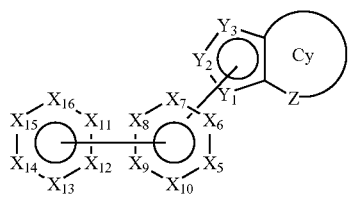

(VI)

wherein

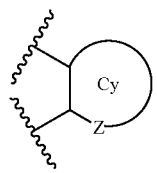

is selected from the group consisting of

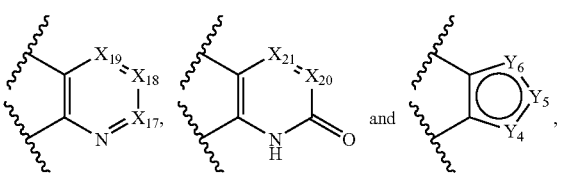

where $X_{17}$-$X_{21}$ are independently selected from the group consisting of C, $CR_1$ or N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, substituted or unsubstituted alkylsulfonyl, acyl, aliphatic, substituted aliphatic, aryl, heteroaryl, and heterocyclic; $Y_4$ is O, N or NH; $Y_5$-$Y_6$ are independently selected from the group consisting of C, $CR_1$, O, S, N or NH; n is 1, 2 or 3, preferably 1 or 2; and $Y_1$-$Y_3$ are as defined in the first embodiment.

Representative compounds according to the invention are those selected from the Table A below or its geometric isomers, enantiomers, diastereomers, racemates, pharmaceutically acceptable salts, prodrugs and solvates thereof:

TABLE A

| Compound # | Structure |
|---|---|
| 1 | 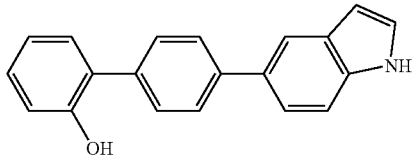 |
| 2 | 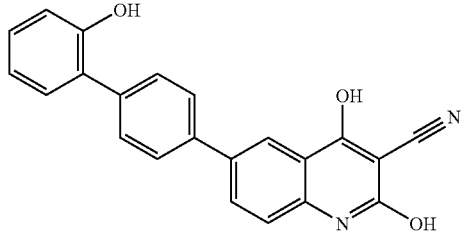 |
| 3 | 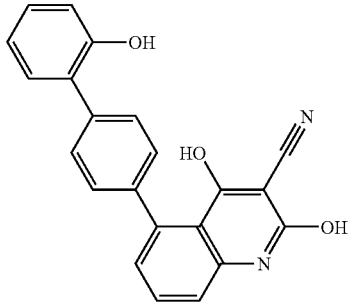 |
| 4 | 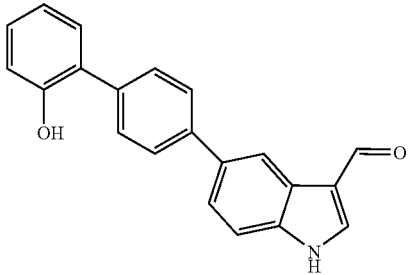 |
| 5 | 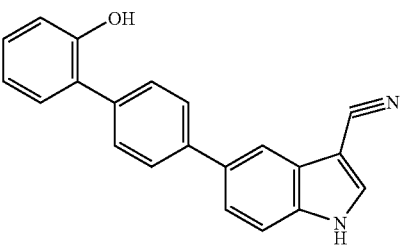 |
| 6 | 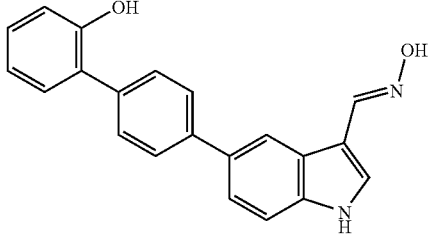 |
| 7 | 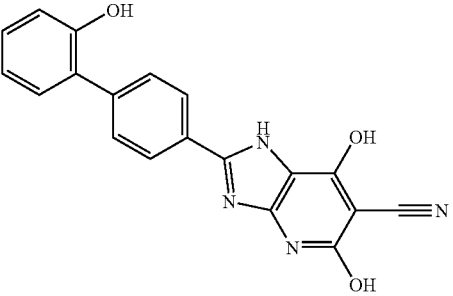 |
| 8 | 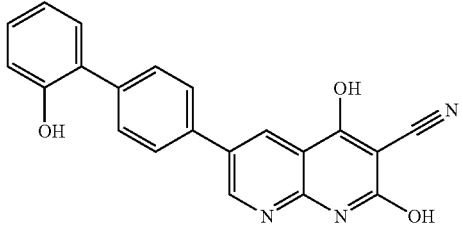 |
| 9 | 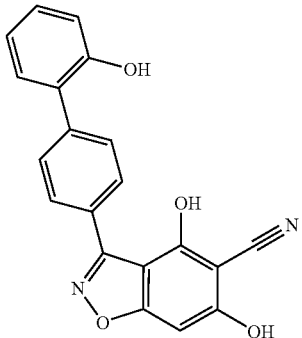 |

TABLE A-continued

| Compound # | Structure |
|---|---|
| 10 | 2'-hydroxy-biphenyl linked to 4-position of 2,4-dihydroxy-3-cyano-1,5-naphthyridine |
| 11 | 2'-hydroxy-biphenyl linked to 2-position of 3-cyano-6,8-dihydroxy-pyrido[2,3-b]pyrazine |
| 12 | 2',4'-dihydroxy-biphenyl linked to 5-position of 1H-indole |
| 13 | 2',4'-dihydroxy-biphenyl linked to 6-position of 3-cyano-2,4-dihydroxyquinoline |
| 14 | 2',4'-dihydroxy-biphenyl linked to 5-position of 3-cyano-2,4-dihydroxy-4a,8a-dihydroquinoline |
| 15 | 2',4'-dihydroxy-biphenyl linked to 5-position of 1H-indole-3-carbaldehyde |
| 16 | 2',4'-dihydroxy-biphenyl linked to 5-position of 1H-indole-3-carbonitrile |
| 17 | 2',4'-dihydroxy-biphenyl linked to 5-position of 1H-indole-3-carbaldehyde oxime |
| 18 | 2',4'-dihydroxy-biphenyl linked to 2-position of 6-cyano-5,7-dihydroxy-3H-imidazo[4,5-b]pyridine |
| 19 | 2',4'-dihydroxy-biphenyl linked to 6-position of 3-cyano-2,4-dihydroxy-1,8-naphthyridine |

TABLE A-continued

| Compound # | Structure |
|---|---|
| 20 | [structure: biphenyl with HO groups connected to isoxazolo-pyridine bearing CN and OH] |
| 21 | [structure: biphenyl with HO groups connected to naphthyridine bearing OH, CN, OH] |
| 22 | [structure: biphenyl with HO groups connected to pyrido-pyrazine bearing OH, CN, OH] |

Accordingly, the compounds of the invention can be employed for prevention or treatment of insulin resistance associated with obesity, glucose intolerance, diabetes mellitus, hypertension and ischemic diseases of the large and small blood vessels. The compounds of the present invention may also be employed in the treatment, prevention or control of a number of conditions that accompany Type 2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated, as well as metabolic syndrome and its component conditions including hypertension, obesity and dislipidemia (including hypertriglyceridemia, hypercholesterolemia and low HDL), and other maladies such as non-cardiac ischemia, infection and cancer. Further, the compounds of the invention are useful in oncology and treating cancers.

Lowering of blood pressure has been reported to be a consequence of AMPK activation (Buhl, E. S. et. al. Long-term AICAR administration reduces metabolic disturbances and lowers blood pressure in rats displaying feature of the insulin resistance syndrome. Diabetes, 51: 2199 (2002)), therefore activation of AMPK might have beneficial effects in hypertension. Through combination of some or all of the above-mentioned effects stimulation of AMPK is expected to reduce the incidence of cardiovascular diseases (e.g. MI, stroke). Increased fatty acid synthesis is a characteristic of many tumor cells, therefore decreased synthesis of fatty acids through activation of AMPK can be useful as a cancer therapy. Stimulation of AMPK has been shown to stimulate production of ketone bodies from astrocytes (Blazquez, C. et. al. The AMP-activated protein kinase is involved in the regulation of ketone body production by astrocytes. J. Neurochem., 73: 1674 (1999)), and might therefore be a strategy to treat ischemic events in the brain. Stimulation of AMPK has been shown to stimulate expression of uncoupling protein 3 (UCP3) in skeletal muscle (Zhou, M. et. al. UCP-3 expression in skeletal muscle: effects of exercise, hypoxia, and AMP-activated protein kinase. Am. J. Physiol. Endocrinol. Metab., 279: E622 (2000)) and might therefore be a way to prevent damage from reactive oxygen species. Endothelial NO synthase (eNOS) has been shown to be activated through AMPK mediated phosphorylation (Chen, Z.-P., et. al. AMP-activated protein kinase phosphorylation of endothelial NO synthase. FEBS Letters, 443: 285 (1999)), therefore AMPK activation can be used to improve local circulatory systems.

The compounds are also useful in treating cancer, as an anti-neoplastic agent. Cancers include solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney and other urinary tissues, eye brain and central nervous system, thyroid and other endocrine gland, Hodgkin's disease, non-Hodgkin's lymphomas, multiple myeloma and hematopoietic malignancies including leukemias and lymphomas including lymphocytic, granulocytic and monocytic.

Disorders that may be regulated by activation of AMPK are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively ameliorate disorders regulated by ghrelin at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating diabetes and/or obesity is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM.

In one embodiment, the concentration of the compound in the patient's plasma is maintained at about 2500 nM. In one embodiment, the concentration of the compound in the patient's plasma is maintained at about 5000 nM. In one embodiment, the concentration of the compound in the patient's plasma is maintained at about 25,000 nM. In one embodiment, the concentration of the compound in the patient's plasma is maintained between about 5,000 nM to about 25,000 nM. The optimal amount of the compound that should be administered to the patient in the practice of the present invention will depend on the particular compound used.

Definitions

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, (e.g., double and/or triple bonds). An aliphatic group may be straight chained, branched or cyclic, contain carbon, hydrogen or, optionally, one or more heteroatoms and may be substituted or unsubstituted. An aliphatic group preferably contains between about 1 and about 24 atoms, more preferably between about 4 to about 24 atoms, more preferably between about 4-12 atoms, more typically between about 4 and about 8 atoms.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "carbonyl", whether used alone or with other terms, such as "alkoxycarbonyl", denotes (C=O).

The term "carbanoyl", whether used alone or with other terms, such as "arylcarbanoylyalkyl", denotes C(O)NH.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, aminocarbonylcycloalkyl, aminocarbonylheterocyclyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —CH$_2$—CH$_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl", "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The term "compound" is defined herein to include pharmaceutically acceptable salts, solvates, hydrates, polymorphs, enantiomers, diastereoisomers, racemates and the like of the compounds having a formula as set forth herein.

The term "treatment" refers to any process, action, application, therapy, or the like, wherein a mammal, including a human being, is subject to medical aid with the object of improving the mammal's condition, directly or indirectly.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., *Journal of Drug Deliver Reviews,* 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 30 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods and Examples

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

5-(2-Methoxybiphenyl)-1H-indole (2)

To a solution of 1 (0.052 mg, 0.26 mmol) in 3.5 mL of dimethoxyethane and water (3:0.5) were added 2-methoxybiphenylboronic acid (0.09 g, 0.39 mmol), barium hydroxide (0.12 g, 0.39 mmol) and 2 mol % of Pd(PPh$_3$)$_4$, under inert atmosphere. The reaction mixture was heated at 85° C. After 6 h, the solution was cooled to room temperature and filtered. Residue was washed with ethyl acetate and combined filtrate was concentrated under reduced pressure. The crude residue was purified by silica gel column chromatography to give 45 mg of 2: $^1$H NMR (CDCl$_3$, 400 MHz) δ 8.19 (br s, 1H), 7.90 (s, 1H), 7.70 (m, 2H), 7.62 (m, 2H), 7.49 (m, 2H), 7.39 (m, 2H), 7.05 (m, 2H), 6.61 (s, 1H), 3.84 (s, 3H).

5-(2-Hydroxybiphenyl)-1H-indole (3) [Compound 1]

To a solution of 2 (0.025 g, 0.084 mmol) in 4 mL of dichloromethane was added 0.25 mL of 1.0 M solution of boron tribromide in dichloromethane at 0° C. Reaction mixture was allowed to warm to room temperature and allowed to stir at this temperature overnight. Upon completion, reaction mixture was diluted with 20 mL of dichloromethane and washed with saturated sodium bicarbonate (2×15 mL), water (2×15 mL), brine (1×10 mL), dried (Na$_2$SO$_4$) and concentrated in vacuo. The crude residue was purified by silica gel column chromatography to give 10 mg of 3. MS (ES+ve) m/z 286.

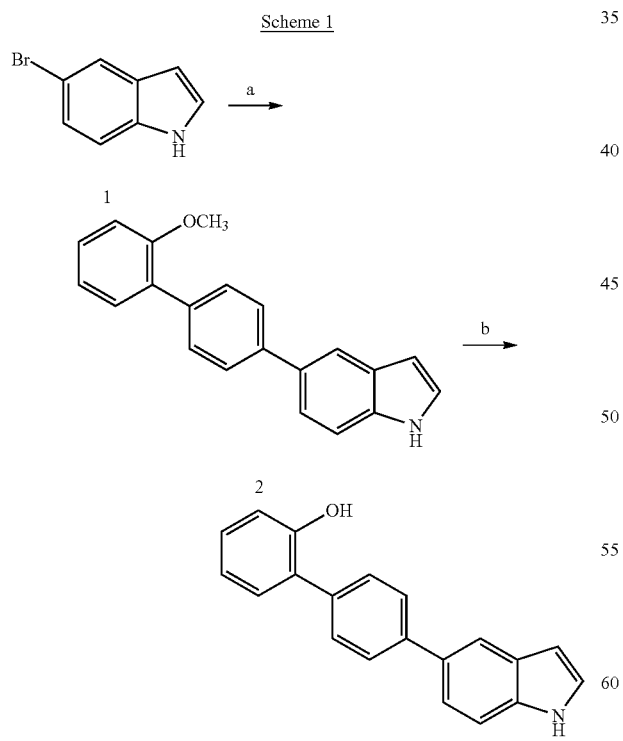

Scheme 1 a. 2-methoxybiphenylboronic acid, Pd(PPh$_3$)$_4$, Ba(OH)$_2$, DME: H$_2$O; b. BBr$_3$, CH$_2$Cl$_2$

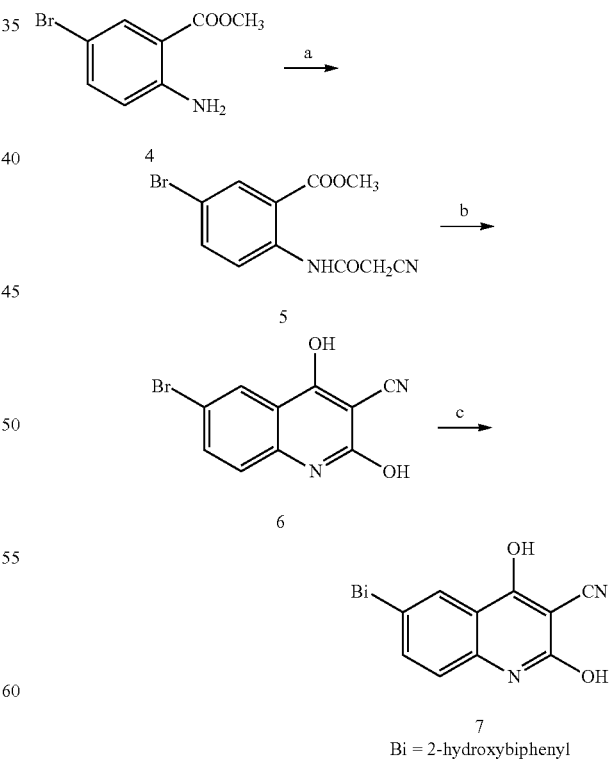

Scheme 2 a. CNCH$_2$COOH, oxalyl chloride, Et$_3$N, CH$_2$Cl$_2$ or CNCH$_2$COOH, HATU, DIPEA, CH$_2$Cl$_2$; b. KHMDS (0.5 M), THF; c. 2-Hydroxybiphenylboronic acid, Pd tetrakis, cesium carbonate, DME: Toluene: EtOH: H$_2$O (10:1:3:6)

Methyl-2-(2-cyanoacetamido)-5-bromobenzoate (5)

The title compound can be prepared by two alternative methods:

A) To a solution of 4 (1.00 g, 4.35 mmol) in 16 mL of dichloromethane was added triethylamine (1.32 g, 13.05 mmol) and the reaction mixture was cooled to 0° C. To the above solution was added cyanoacetyl chloride (10.87 mmol) (prepared freshly from cyanoacetic acid (0.92 g, 10.87 mmoles) and oxalyl chloride (10.87 mmoles) in 16 mL dichloromethane and catalytic amounts of DMF). The reaction mixture was allowed to warm at room temperature. After completion, dichloromethane was removed in vacuo and the crude residue was taken up in ethylacetate (50 mL) and the organic layer was washed with saturated sodium bicarbonate (2×25 mL), water (2×25 mL), brine (1×15 mL), dried ($Na_2SO_4$) and concentrated in vacuo. The crude residue was purified by silica gel column chromatography to give almost quantitative yield of 5. $^1$H NMR ($CDCl_3$, 400 MHz) δ 8.41 (d, J=9.2 Hz, 1H), 8.08 (d, J=2.4 Hz, 1H), 7.58 (dd, J=2.4 Hz, 9.2 Hz, 1H), 3.58 (s, 2H).

B) To a solution of cyanoacetic acid (0.92 g, 10.87 mmol) in 20 mL dichloromethane and dimethylacetamide (4:1) was added HATU (4.13 g, 10.87 mmol) and diisopropylethyl amine (1.75 g, 13.49 mmol) and the reaction mixture stirred for 15 minutes. To the above solution was added 4 (1.00 g, 4.35 mmol) in 10 mL dichloromethane and the reaction mixture heated at 60° C. After completion, the reaction mixture was cooled to room temperature and was washed with saturated sodium bicarbonate (2×25 mL), water (2×25 mL), brine (1×15 mL), dried ($Na_2SO_4$) and concentrated in vacuo. The crude residue was purified by silica gel column chromatography to give almost quantitative yield of 5. $^1$H NMR ($CDCl_3$+$CD_3OD$, 400 MHz) δ 8.41 (d, J=9.2 Hz, 1H), 8.08 (d, J=2.4 Hz, 1H), 7.58 (dd, J=2.4 Hz, 9.2 Hz, 1H), 3.58 (s, 2H).

6-Bromo-2,4-dihydroxyquinoline-3-carbonitrile (6)

A stirred solution of 5 (0.15 g, 0.48 mmol) in 7 mL of THF was cooled to −78° C. To the cooled solution was added 2.41 mL of KHMDS (0.5M) solution. The reaction was allowed to warm to room temperature. Upon completion, the reaction mixture was concentrated in vacuo. To the residue was added 10 mL of water. The aqueous layer was washed with diethyl ether (2×15 mL) and then acidified with 1M HCl. The precipitated solid was filtered and washed with water and ether to give 60 mg of 6. $^1$H NMR ($CD_3OD$, 400 MHz) δ 8.13 (d, J=2.4 Hz, 1H), 7.71 (dd, J=2.4 Hz, 9.2 Hz, 1H), 7.21 (d, J=9.2 Hz, 1H); MS (Es+ve) m/z 265, (Es−ve) m/z 263.

6-(2-Hydroxybiphenyl)-2,4-dihydroxyquinoline-3-carbonitrile (7) [Compound 2]

To a solution of 6 (0.037 g, 0.140 mmol) in 4.3 mL of dimethoxyethane: toluene: ethanol:water (10:1:3:6) was added 2-hydroxybiphenylboronic acid (0.045 g, 0.210 mmol), cesium carbonate (0.091 g, 0.28 mmol) and 2 mol % palladium tetrakis under inert atmosphere. The reaction mixture was heated at 100° C. overnight. After completion, reaction mixture was cooled to room temperature and was concentrated in vacuo. The residue was taken up in 10 mL water and the aqueous layer was washed with ethylacetate (2×15 mL) and the aqueous layer was acidified using 1M HCl. The precipitated solid was filtered and washed with water and ether to give 18 mg of 7. $^1$H NMR ($CD_3OD$, 400 MHz) δ 8.36 (d, J=1.6 Hz, 1H), 8.05 (dd, J=2.4 Hz, 9.2 Hz, 1H), 7.75 (m, 4H), 7.46 (d, J=8.4 Hz, 1H), 7.34 (m, 1H), 7.18 (m, 1H), 6.94 (m, 2H); MS (Es+ve) m/z 354; (Es−ve) m/z 353.

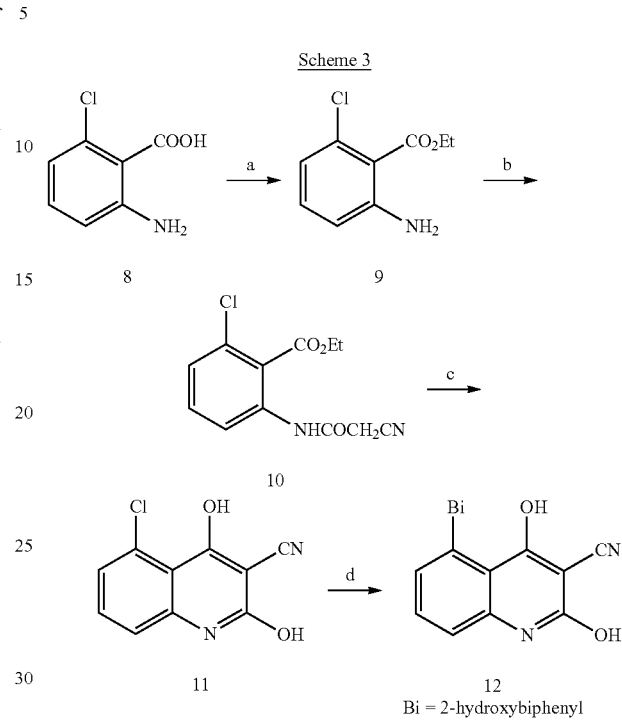

Scheme 3 a. 1,1'-Carbonyldiimidazole, THF; NaOEt, EtOH; b. $CNCH_2COOH$, oxalyl chloride, $Et_3N$, $CH_2Cl_2$ or $CNCH_2COOH$, HATU, DIPEA, $CH_2Cl_2$; c. KHMDS (0.5 M), THF; d. 2-Hydroxybiphenylboronic acid, $Pd(OAc)_2$, $K_3PO_4$, S-Phos, DME: Toluene: EtOH: $H_2O$ (10:1:3:6)

Ethyl-2-amino-6-chlorobenzoate (9)

To a solution of 8 (0.50 g, 2.91 mmol) in 7 mL of THF was added 1,1'-carbonyldiimidazole (0.52 g, 3.20 mmol) and the reaction mixture was stirred for 4 h. On completion, the reaction mixture was concentrated in vacuo and the residual solid was dissolved in 50 mL dichloromethane and was washed with saturated sodium bicarbonate (2×25 mL), water (2×25 mL), brine (1×15 mL), dried ($Na_2SO_4$) and concentrated in vacuo to give 0.48 g of solid. The solid was dissolved in 1 mL ethanol and 5 mL THF and sodium ethoxide (0.18 g) was added and the reaction mixture heated at 70° C. for 1 h. On completion, the solvent was removed in vacuo and the residue was dissolved in ethyl acetate, washed with water (2×15 mL), brine (1×15 mL), dried ($Na_2SO_4$) and concentrated in vacuo to give 0.29 g of practically pure 9. An analytical sample of 9 was prepared by purification using silica gel column chromatography $^1$H NMR ($CDCl_3$, 400 MHz) δ 7.07 (m, 1H), 6.74 (d, J=8.0 Hz, 1H), 6.57 (d, J=8.0 Hz, 1H).

Ethyl-2-(2-cyanoacetamido)-4-chlorobenzoate (10)

The title compound was prepared in analogous manner as described for 5. Thus, starting from 9 (0.05 g, 0.35 mmol) following the above described procedure gave 25 mg of pure 10. $^1$H NMR ($CDCl_3$, 400 MHz) δ 9.71 (br s, 1H), 8.19 (d, J=8.4 Hz, 1H), 7.40 (m, 1H), 7.26 (m, 1H), 4.51 (q, J=7.2 Hz, 2H), 3.54 (s, 2H), 1.45 (t, J=7.2 Hz, 3H).

5-Chloro-2,4-dihydroxyquinoline-3-carbonitrile (11)

The title compound was prepared in analogous manner as described for 6. Thus, starting from 10 (0.30 g, 1.12 mmol)

following the above described procedure gave 125 mg of pure 11. MS (Es+ve) m/z 221, (Es−ve) m/z 219.

5-(2-Hydroxybiphenyl)-2,4-dihydroxyquinoline-3-carbonitrile (12) [Compound 3]

The title compound was prepared in analogous manner as described for 7. Thus, starting from 11 (0.043 g, 0.195 mmol) following the above described procedure, 2 mol % Pd(OAc)$_2$, S-phos (4 mol %) and 1.0M K$_3$PO$_4$ (3 eq) were used instead of Pd(PPh$_3$)$_4$ and cesium carbonate gave 10 mg of pure 12. $^1$H NMR (DMSO-d$_6$, 400 MHz) δ 10.01 (s, 1H), 9.49 (s, 1H), 7.41 (d, J=8.0 Hz, 2H), 7.28 (m, 2H), 7.13 (m, 4H), 6.93 (m, 2H), 6.61 (d, J=7.2 Hz, 1H); MS (Es+ve), m/z 354 (Es−ve) m/z 353.

mL). The organic layer was separated and washed successively with water (2×20 mL), brine (1×15 mL), dried (Na$_2$SO$_4$) and concentrated to give 0.75 g 14 (mixture of geometric isomers). $^1$H NMR (CDCl$_3$, 400 MHz) δ 8.06 (s, 1H), 7.51 (d, J=8.4 Hz, 2H), 7.43 (d, J=8.4 Hz, 2H).

4-Bromobenzaldehyde-α-chlorooxime (15)

To a stirred solution of 14 (0.75 g, 3.75 mmol) in 16 mL DMF was added N-chlorosuccinimide (0.50 g, 3.75 mmol) slowly at 0° C. The reaction mixture was warmed at 50° C. for 1 h and was poured on to crushed ice. Diluted with water and the precipitated solid washed with water and dried to give 0.9 g of practically pure 15. $^1$H NMR (CDCl$_3$, 400 MHz) δ 7.56 (d, J=8.4 Hz, 2H), 7.37 (d, J=8.4 Hz, 2H).

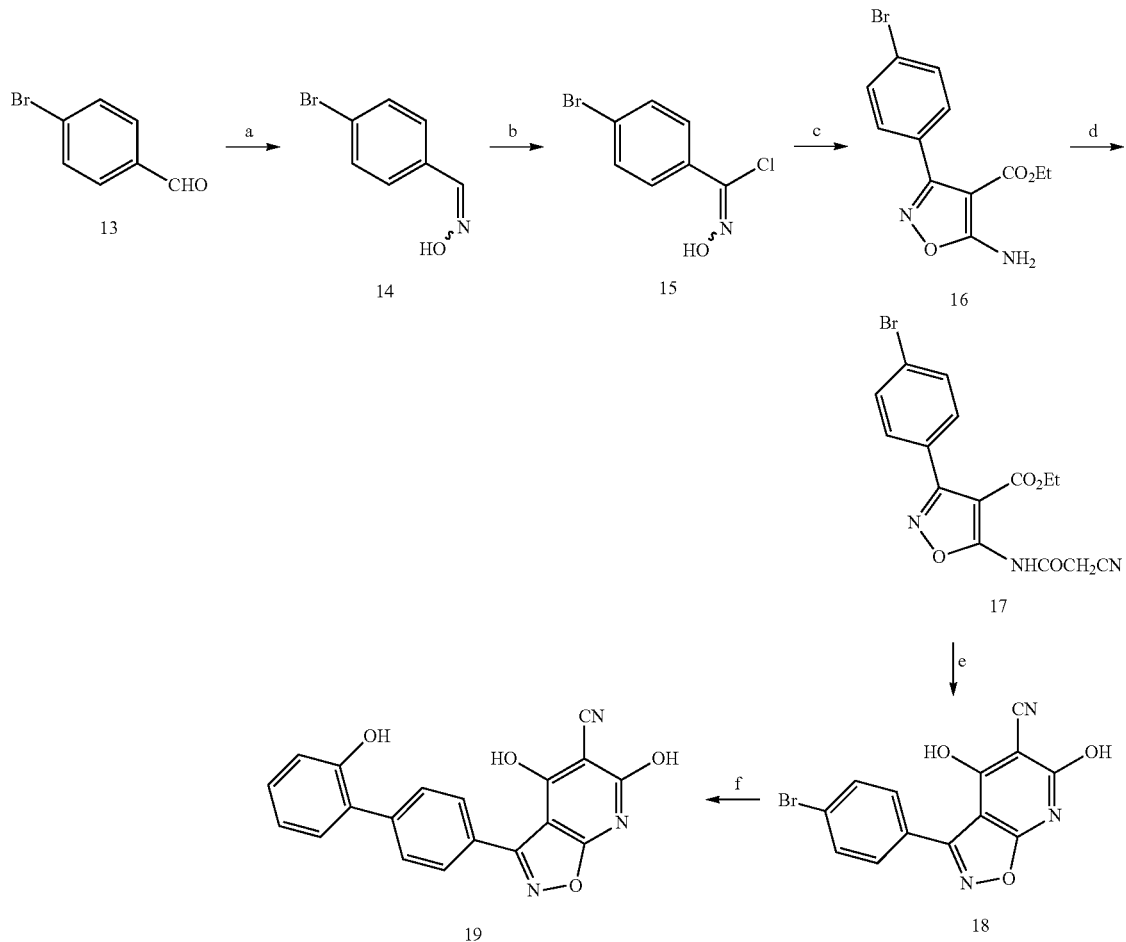

Scheme 4 a. NH$_2$OH·HCl, CH$_3$COONa, MeOH; b. NCS, DMF; c. Ethylcyanoacetate, NaOEt, EtOH; d. CNCH$_2$COOH, (COCl)$_2$, Et$_3$N, CH$_2$Cl$_2$, DMF (Cat.); e. KHMDS (0.5 M), THF; f. 2-Hydroxybenzeneboronic acid, Pd tetrakis, cesium carbonate, DME: Tol: EtOH: H$_2$O (10:1:3:6)

4-Bromobenzaldehyde oxime (14)

To a stirred solution of hydroxylamine hydrochloride (0.47 g, 6.76 mmol) in 10 mL methanol was added sodium acetate (0.56 g, 6.76 mmol) and the reaction mixture was stirred for 15 min. 13 ((1.00 g, 5.41 mmol) was added and the reaction mixture was heated at 70° C. for 4 h. On completion, the reaction mixture was concentrated in vacuo. The solid residue was dissolved in dichloromethane (25 mL) and water (20

Ethyl-5-amino-3-(4-bromophenyl)isoxazole-4-carboxylate (16)

To a solution of ethylcyanoacetate (0.11 mL, 1.1 mmol) in 4 mL ethanol cooled to 0° C. was added sodium ethoxide (0.07 g, 1.1 mmol) and the reaction mixture was stirred at this temperature for 15 min. To the above solution was added 15 (0.24 g, 1.00 mmol) in 3 mL of ethanol at 0° C. and the reaction mixture was allowed to warm to room temperature.

The reaction mixture was stirred at room temperature overnight and was concentrated in vacuo. The crude mixture was dissolved in ethylacetate (25 mL) and water (20 mL). Organic layer was separated and washed with water (2×20 mL), saturated NH$_4$Cl (2×15 mL), brine (1×15 mL, dried (Na$_2$SO$_4$) to give 0.3 g of practically pure 16. If required, the solid can be further purified by triturating with 15-20% ethylacetate:hexane mixture. Analytical sample was obtained by purification with silica gel column chromatography. $^1$H NMR (CDCl$_3$, 400 MHz) δ 7.55 (m, 4H), 6.10 (br s, 2H), 4.22 (q, J=7.2 Hz, 2H), 1.20 (t, J=7.2 Hz, 3H); MS (Es+ve) m/z 311 (Es−ve) m/z 309.

Ethyl-5-(2-cyanoacetamido)-3-(4-bromophenyl)isoxazole-4-carboxylate (17)

The title compound was prepared in analogous manner as described for 5. Thus, starting from 16 (0.10 g, 0.323 mmol) following the above described procedure gave 90 mg of pure 17. $^1$H NMR (CDCl$_3$, 400 MHz) δ 7.35 (d, J=7.2 Hz, 2H), 7.31 (d, J=7.2 Hz, 2H), 4.05 (q, J=7.2 Hz, 2H), 3.39 (s, 1H), 1.20 (t, J=7.2 Hz, 3H).

3-(4-Bromophenyl)-4,6-dihydroxyisoxazolo[5,4-b]pyridine-5-carbonitrile (18)

The title compound was prepared in analogous manner as described for 6. Thus, starting from 17 (0.06 g, 0.159 mmol) following the above described procedure gave 25 mg of pure 18. $^1$H NMR (CD$_3$OD, 400 MHz) δ 7.69 (d, J=7.2 Hz, 2H), 7.63 (d, J=7.2 Hz, 2H).

3-(2-Hydroxybiphenyl)-4,6-dihydroxyisoxazolo[5,4-b]pyridine-5-carbonitrile (19) [Compound 9]

The title compound was prepared in analogous manner as described for 7. Thus, starting from 18 (0.022 g) following the above described procedure, 2-hydroxybenzeneboronic acid was used instead of 2-hydroxybiphenylboronic acid, to give 10 mg of pure 19. $^1$H NMR (CD$_3$OD, 400 MHz) δ 7.84 (d, J=8.0 Hz, 2H), 7.76 (d, J=8.0 Hz, 2H), 7.30 (d, J=9.2 Hz, 1H), 7.16-7.2 (m, 1H), 6.88-6.92 (m, 2H).

Scheme 5

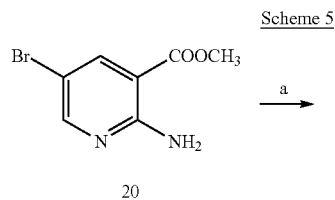

Methyl 2-amino-5-bromopyridine-3-carboxylate (21)

The title compound was prepared in analogous manner as described for 5. Thus, starting from 20 (0.30 g, 1.3 mmol) following the above described procedure gave 313 mg of pure 21.

6-Bromo-2,4-dihydroxy-1,8-naphthyridine-3-carbonitrile (22)

The title compound was prepared in analogous manner as described for 6. Thus, starting from 21 (0.313 g, 1.05 mmol) following the above described procedure gave 106 mg of pure 22. $^1$H NMR (CDCl$_3$, 400 MHz) δ 8.51 (s, 1H), 8.29 (s, 1H); MS (Es+ve) m/z 267, (Es−ve) m/z 265.

6-(2-Hydroxybiphenyl)-2,4-dihydroxy-1,8-naphthyridine-3-carbonitrile (23) [Compound 8]

The title compound was prepared in analogous manner as described for 7. Thus, starting from 22 (0.106 g, 0.398 mmol) following the above described procedure gave 56 mg of pure 23. $^1$H NMR (CDCl$_3$, 400 MHz) δ 11.02 (s, 1H), 9.62 (br s, 1H), 8.92 (s, 1H), 8.75 (s, 1H), 8.56 (s, 1H), 8.19 (s, 1H), 7.77 (m, 1H), 7.65 (m, 1H), 7.25 (m, 1H), 7.19 (m, 1H), 6.95 (m, 2H); MS (Es+ve) m/z 356, (Es−ve) m/z 354.

Scheme 6

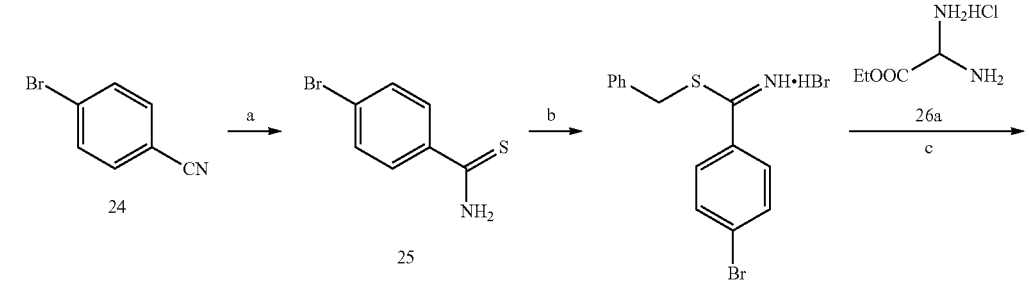

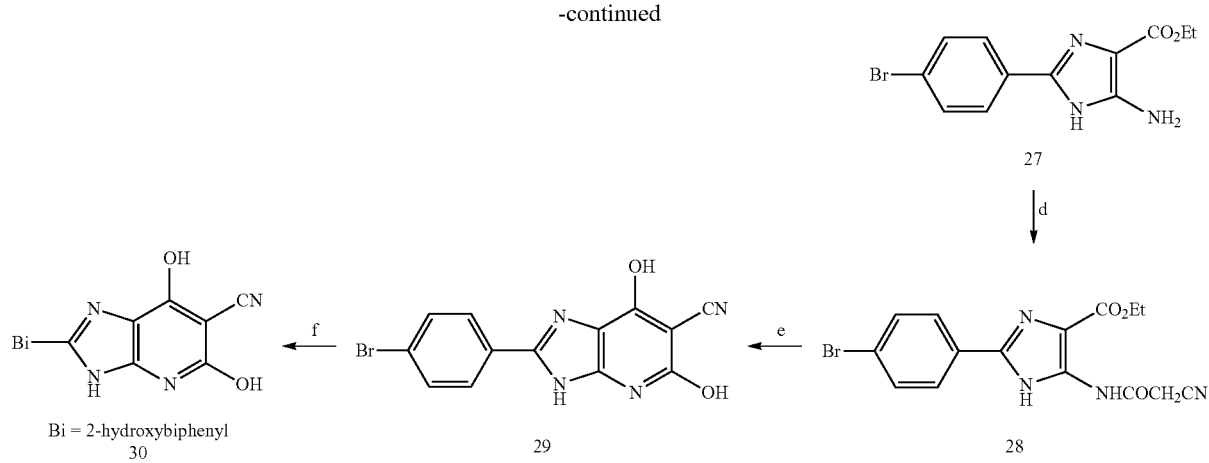

Bi = 2-hydroxybiphenyl a. (EtO)₂PS₂H, H₂O, MW; b. BnBr; c. Pyridine, NH₃, MeOH; d. CNCH₂COOH, (COCl)₂, Et₃N, CH₂Cl₂, DMF (Cat.); e. KHMDS (0.5 M), THF; f. 2-Hydroxybenzeneboronic acid, Pd tetrakis, cesium carbonate, DME: Tol: EtOH: H₂O (10:1:3:6)

Ethyl 5-amino-2-(4-bromophenyl)-1H-imidazole-4-carboxylate (27)

To 24 (1.82 g, 10.0 mmol) in 16 mL water was added diethyldithiophosphoric acid (2.24 g, 12.0 mmol) and the mixture was heated at 80° C. under microwave irradiation for 15 minutes. Upon completion, the reaction mixture was extracted with diethyl ether and then washed with saturated NaHCO₃ (2×20 mL), brine (1×20 mLO, dried (Na₂SO₄), concentrated in vacuo and purified by silica gel column chromatography to give 1.2 g of 25 as a white solid.

To a solution of thioamide 25 (1.40 g, 6.5 mmol) in 15 mL anhydrous chloroform was added benzyl bromide (4.45 g, 26 mmol) and the RM was heated at 80° C. under microwave irradiation for 15 minutes. The reaction mixture was evaporated to dryness and diethyl ether was added in large excess to precipitate 1.6 g of thioiminoether hydrobromide 26. This product was dried under vacuum and used for the next step.

To a solution of 26 (1.00 g, 2.6 mmol) in 10 mL anhydrous dichloromethane was added pyridine (0.205 ml, 2.6 mmol). In another RB flask containing 26a (prepared by a procedure described in literature) (476 mg, 3.1 mmol) in 10 mL anhydrous dichloromethane was added NH₃ in methanol (6.2 mmol). Both reaction mixtures were filtered into a microwave vessel and anhydrous chloroform (10 mL) was added. The reaction mixture was heated to 60° C. in a microwave reactor. The reaction was monitored by TLC and was finished in 10 minutes. The reaction mixture was evaporated to dryness and diethyl ether was added to precipitate 600 mg of 27. The product was filtered, washed with ether and dried under vacuum. MS (Es+ve) m/z 310.

Ethyl 5-(2-cyanoacetamido)-2-(4-bromophenyl)-1H-imidazole-4-carboxylate (28)

The title compound was prepared in analogous manner as described for 5. Thus, starting from 27 (0.3 g, 0.97 mmol) 160 mg of pure 28 was obtained. ¹H NMR (CDCl₃, 400 MHz) δ 7.98 (d, J=7.2 Hz, 2H), 7.65 (d, J=7.2 Hz, 2H), 4.21 (q, 2H), 3.30 (s, 2H), 1.25 (t, 3H). MS (Es+ve) m/z 377.

2-(4-Bromophenyl)-5,7-dihydroxy-3H-imidazo[4,5-b]pyridine-6-carbonitrile (29)

The title compound was prepared in analogous manner as described for 6. Thus, starting from 28 (0.071 g, 0.189 mmol) following the above described procedure gave 25 mg of 29. MS (Es+ve) m/z 331.

3-(2-Hydroxybiphenyl)-4,6-dihydroxyimidazo[5,4-b]pyridine-5-carbonitrile (30) [Compound 7]

The title compound was prepared in analogous manner as described for 7. Thus, starting from 29 (0.022 g, 0.066 mmol) using 2-hydroxybenzeneboronic acid instead of 2-hydroxybiphenylboronic acid, following the above described procedure gave 5 mg of 30. MS (Es+ve) m/z 345, (Es−ve) 343.

Scheme 7

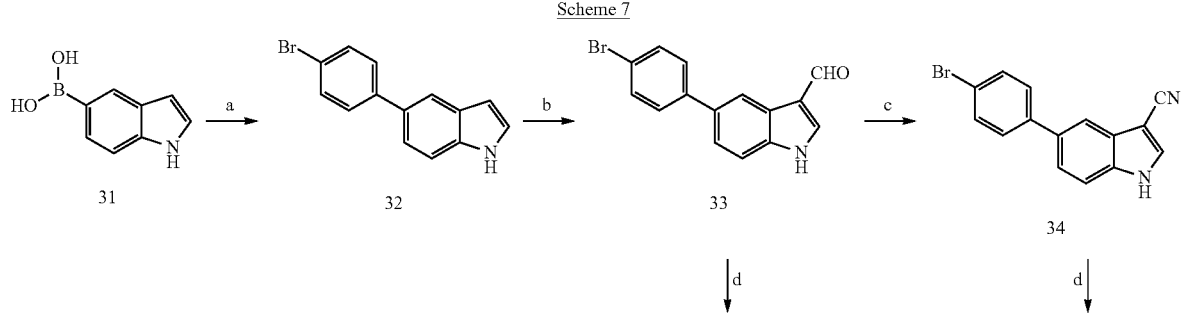

-continued

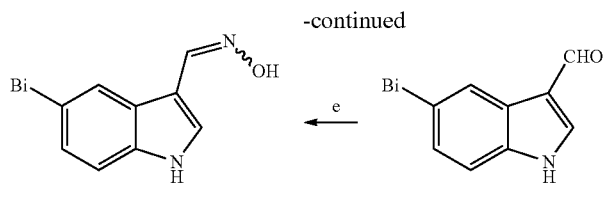 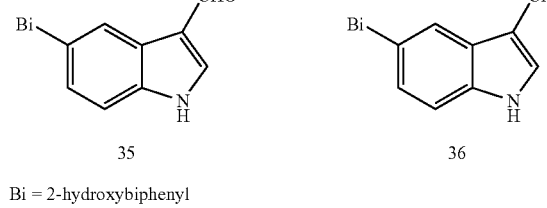

Bi = 2-hydroxybiphenyl a. 4-Bromoiodobenzene, Pd tetrakis, cesium carbonate, DME: H₂O b. DMF, POCl₃; c. NH₄(NO₃)₂, CH₃COOH; d. 2-hydroxybenzeneboronic acid, Pd tetrakis, cesium carbonate, DME: H₂O; e. hydroxylamine hydrochloride, CH₃COONa, MeOH 5-(4-Bromophenyl)-1H-indole (32)

To a solution of 31 (3.093 g, 10.93 mmol) in 30 mL of dimethoxyethane:toluene:ethanol:water (10:1:3:6) was added 4-bromoiodobenzene (1.60 g, 9.94 mmol), barium hydroxide octahydrate (6.312 g, 20.01 mmol) and 5 mol % Pd(PPh₃)₄ under inert atmosphere. The reaction mixture was heated at 90° C. for 3 hours. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na₂SO₄), filtered and concentrated to give crude as red oil. The material was further purified via column chromatography (10%->35% EtOAc in Hexanes) to give 1.7 g of 32 as white solid.

5-(4-Bromophenyl)-1H-indole-3-carbaldehyde (33)

In a 100-ml round-bottom flask is placed 2.8 mL of dimethylformamide (2.74 g, 3.74 mmol). The flask and the content was cooled in an ice-salt bath for about 0.5 hour and 0.86 mL (1.44 g, 94 mmol) of freshly distilled phosphorusoxychloride is subsequently added with stirring to the dimethylformamide dropwise. Then a solution of 1.0 g of 32 (85 mmol) in 1 mL of dimethylformamide is added to the above solution slowly. After the addition, the temperature of the solution is brought to 40° C. and allowed to stir for an hour. At this time, 1N NaOH (10 mL) was added to the reaction mixture dropwise. The resulting mixture is heated rapidly to the boiling point and allowed to cool to room temperature. The resulting precipitate is collected on a filter and the solid was further washed with water. Compound 33 obtained from this procedure was pure enough for the next reaction. MS (Es+ve) m/z 300, (Es-ve) m/z 298.

5-(4-Bromophenyl)-1H-indole-3-carbonitrile (34)

A mixture of 33 (1.35 g 4.50 mmol), diammonium hydrogen phosphate (3.19 g, 23.8 mmol), 1-nitropropane (13.61 g, 152.9 mmol) and glacial acetic acid (10 mL) is refluxed overnight. During the reflux period, the pale-yellow mixture becomes dark red. The volatile reactants and solvents were removed under reduced pressure and an excess of water is then added to the dark residue. After a short time the crude 34 precipitated rapidly. It is separated by filtration washed with hexanes and dried under reduced pressure. Compound 34 was obtained as pale yellow solid in 1.19 g. MS (Es-ve) m/z 295.

5-(2-Hydroxybiphenyl)-1H-indole-3-carbaldehyde (35) [Compound 4]

The title compound was prepared in analogous manner as described for 7. Thus, starting from 33 (1.6 g, 5.3 mmol) and 2-hydroxy benzeneboronic acid instead of 2-hyroxybiphenylboronic acid following the above described procedure gave 1 g of pure 35. ¹H NMR (CDCl₃, 400 MHz) δ 9.80 (s, 1H), 8.39 (s, 1H), 7.79 (s, 1H), 7.61 (d, J=8.4 Hz, 2H), 7.51 (d, J=8.4 Hz, 2H), 7.45 (m, 1H), 7.38 (m, 1H), 7.18 (m, 2H), 7.02 (m, 1H), 6.78 (m, 1H); MS (Es+ve) m/z 312, (Es-ve) m/z 314.

5-(2-Hydroxybiphenyl)-1H-indole-3-carbonitrile (36) [Compound 5]

The title compound was prepared in analogous manner as described for 7. Thus, starting from 34 (1.19 g, 4.00 mmol) and 2-hydroxy benzeneboronic aicd instead of 2-hyroxybiphenylboronic acid following the above described procedure gave 710 mg of pure 36. ¹H NMR (CDCl₃, 400 MHz) δ 8.76 (br s, 1H), 8.00 (s, 1H), 7.75 (m, 3H), 7.57 (m, 4H), 7.29 (m, 2H), 7.05 (m, 2H); MS (Es-ve) m/z 309.

5-(2-Hydroxybiphenyl)-1H-indole-3-carbaldehyde oxime (37) [Compound 6]

To hydroxylamine hydrochloride (0.014 g, 0.20 mmol) in 3 mL methanol was added sodium acetate (0.016 mg, 0.20 mmol) and the reaction mixture stirred at room temperature for 15 min. To this mixture was added 35 (0.05 g, 0.16 mmol) in 2 mL methanol and the reaction mixture refluxed overnight. Reaction mixture concentrated in vacuo and the residue dissolved in dichloromethane, washed with water (2×15 mL), brine (1×15 mL), dried (Na₂SO₄) to give 30 mg of 37 as a pale yellow solid as a mixture of geometric isomers (1:1) MS (Es+ve) m/z 329, MS (Es-ve) m/z 327.

Scheme 8

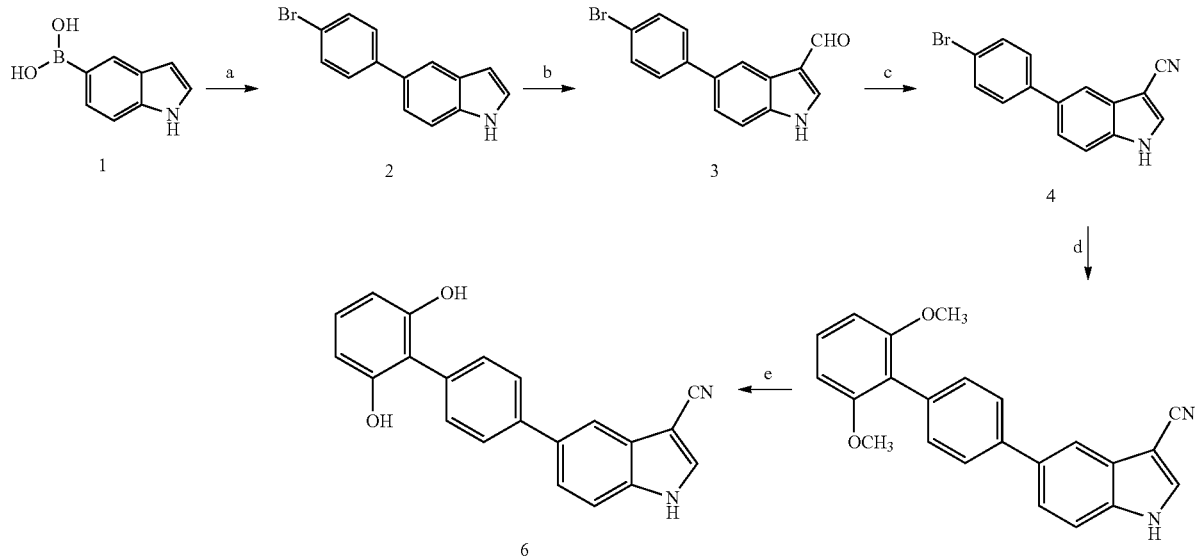

Reagents and Conditions: a. 4-Bromoiodobenzene, Pd tetrakis, cesium carbonate, DME: H₂O; b. DMF, POCl₃; c. NH₄(NO₃)₂, CH₃COOH; d. 2,5-dihydroxybenzeneboronic acid, Pd tetrakis, cesium carbonate, DME: H₂O; e. BBr₃, CH₂Cl₂

5-(4-Bromophenyl)-1H-indole (2)

To a solution of 1 (3.093 g, 10.93 mmol) in 30 mL of dimethoxyethane:toluene:ethanol:water (10:1:3:6) was added 4-bromoiodobenzene (1.60 g, 9.94 mmol), barium hydroxide octahydrate (6.312 g, 20.01 mmol) and 5 mol % Pd(PPh₃)₄ under inert atmosphere. The reaction mixture was heated at 90° C. for 3 hours.

After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na₂SO₄), filtered and concentrated to give crude as red oil. The material was further purified via column chromatography (10%->35% EtOAc in Hexanes) to give 1.7 g of 2 as white solid.

5-(4-Bromophenyl)-1H-indole-3-carbaldehyde (3)

In a 100-ml round-bottom flask is placed 2.8 mL of dimethylformamide (2.74 g, 3.74 mmol). The flask and the content was cooled in an ice-salt bath for about 0.5 hour and 0.86 mL (1.44 g, 94 mmol) of freshly distilled phosphorusoxychloride is subsequently added with stirring to the dimethylformamide dropwise. Then a solution of 1.0 g of 2 (85 mmol) in 1 mL of dimethylformamide is added to the above solution slowly. After the addition, the temperature of the solution is brought to 40° C. and allowed to stir for an hour. At this time, 1N NaOH (10 mL) was added to the reaction mixture dropwise. The resulting mixture is heated rapidly to the boiling point and allowed to cool to room temperature. The resulting precipitate is collected on a filter and the solid was further washed with water. Compound 3 obtained from this procedure was pure enough for the next reaction. MS (Es+ve) m/z 300, (Es−ve) m/z 298.

5-(4-Bromophenyl)-1H-indole-3-carbonitrile (4)

A mixture of 3 (1.35 g 4.50 mmol), diammonium hydrogen phosphate (3.19 g, 23.8 mmol), 1-nitropropane (13.61 g, 152.9 mmol) and glacial acetic acid (10 mL) is refluxed overnight. During the reflux period, the pale-yellow mixture becomes dark red. The volatile reactants and solvents were removed under reduced pressure and an excess of water is then added to the dark residue. After a short time the crude 4 precipitated rapidly. It is separated by filtration washed with hexanes and dried under reduced pressure. Compound 34 was obtained as pale yellow solid in 1.19 g. MS (Es−ve) m/z 295.

5-(2,6-Dimethoxybiphenyl)-1H-indole-3-carbonitrile (5)

To a solution of 4 (1.00 g, 3.38 mmol) in 10 mL of dimethoxyethane:toluene:ethanol:water (10:1:3:6) was added 2,6-dimethoxybromobenzene (1.14 g, 4.39 mmol), cesium carbonate (2.75 g, 8.45 mmol) and 5 mol % Pd(PPh₃)₄ under inert atmosphere. The reaction mixture was heated at 90° C. for O/N. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na₂SO₄), filtered and concentrated to give crude as red oil. The material was further purified via column chromatography (10%->35% EtOAc in Hexanes) to give 0.65 g of 5 as biege solid.

5-(2,6-Dihydroxybiphenyl)-1H-indole-3-carbonitrile (6)

To a stirring solution of 4 (1.3 g, 3.7 mmol) in CH₂Cl₂ (20 mL) at 0° C. was added BBr₃ (1.0 mL, 12.1 mmol). The reaction mixture was allowed to warm up to room temperature and was allowed to stir for 1 hour. At this time, the reaction was quenched with the addition of water (10 mL). Solid will precipitate from the mixture, which was obtained via filtration and was purified via chromatography (30%→70%→100% Ethyl Acetate:Hexanes) to obtain 451 mg of the final product 6.

Scheme 9

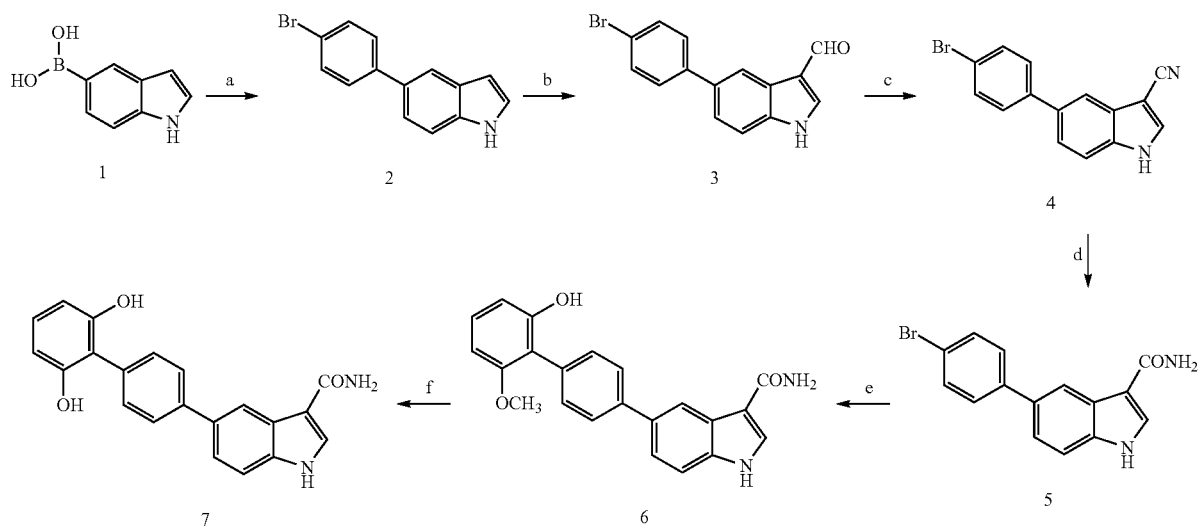

a. 4-Bromoiodobenzene, Pd tetrakis, cesium carbonate, DME: H₂O; b. DMF, POCl₃; c. NH₄(NO₃)₂, CH₃COOH; d. H₂O₂ 1N NaOH, MeOH; e. 2,6-Dimethoxybenzeneboronic acid, Pd tetrakis, cesium carbonate, DME: H₂O; f. BBr₃, DCM

5-(4-Bromophenyl)-1H-indole (2)

To a solution of 1 (3.093 g, 10.93 mmol) in 30 mL of dimethoxyethane:toluene:ethanol:water (10:1:3:6) was added 4-bromoiodobenzene (1.60 g, 9.94 mmol), barium hydroxide octahydrate (6.312 g, 20.01 mmol) and 5 mol % Pd(PPh$_3$)$_4$ under inert atmosphere. The reaction mixture was heated at 90° C. for 3 hours. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na$_2$SO$_4$), filtered and concentrated to give crude as red oil. The material was further purified via column chromatography (10%->35% EtOAc in Hexanes) to give 1.7 g of 2 as white solid.

5-(4-Bromophenyl)-1H-indole-3-carbaldehyde (3)

In a 100-ml round-bottom flask is placed 2.8 mL of dimethylformamide (2.74 g, 3.74 mmol). The flask and the content was cooled in an ice-salt bath for about 0.5 hour and 0.86 mL (1.44 g, 94 mmol) of freshly distilled phosphorusoxychloride is subsequently added with stirring to the dimethylformamide dropwise. Then a solution of 1.0 g of 2 (85 mmol) in 1 mL of dimethylformamide is added to the above solution slowly. After the addition, the temperature of the solution is brought to 40° C. and allowed to stir for an hour. At this time, 1N NaOH (10 mL) was added to the reaction mixture dropwise. The resulting mixture is heated rapidly to the boiling point and allowed to cool to room temperature. The resulting precipitate is collected on a filter and the solid was further washed with water. Compound 3 obtained from this procedure was pure enough for the next reaction. MS (Es+ve) m/z 300, (Es–ve) m/z 298.

5-(4-Bromophenyl)-1H-indole-3-carbonitrile (4)

A mixture of 3 (1.35 g 4.50 mmol), diammonium hydrogen phosphate (3.19 g, 23.8 mmol), 1-nitropropane (13.61 g, 152.9 mmol) and glacial acetic acid (10 mL) is refluxed overnight. During the reflux period, the pale-yellow mixture becomes dark red. The volatile reactants and solvents were removed under reduced pressure and an excess of water is then added to the dark residue. After a short time the crude 4 precipitated rapidly. It is separated by filtration washed with hexanes and dried under reduced pressure. Compound 34 was obtained as pale yellow solid in 1.19 g. MS (Es–ve) m/z 295.

5-(4-Bromophenyl)-1H-indole-3-carboxamide (5)

A solution of 4 (1.00 g, 3.38 mmol) in ethanol was treated with hydrogen peroxide (30%) and 1N NaOH. On completion of reaction solvent was removed and the resultant solid was washed with organic solvents to give pure 5 as a beige colored solid.

5-(2,6-Dimethoxybiphenyl)-1H-indole-3-carboxamide (6)

To a solution of 5 (1.00 g, 3.18 mmol) in 10 mL of dimethoxyethane:toluene:ethanol:water (10:1:3:6) was added 2,6-dimethoxybromobenzene (1.10 g, 4.14 mmol), cesium carbonate (2.59 g, 7.95 mmol) and 5 mol % Pd(PPh$_3$)$_4$ under inert atmosphere. The reaction mixture was heated at 90° C. for O/N. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na$_2$SO$_4$), filtered and concentrated to give crude as red oil. The material was further purified via column chromatography (10%->35% EtOAc in Hexanes) to give 0.60 g of 6 as biege solid.

5-(2,6-Dihydroxybiphenyl)-1H-indole-3-carboxamide (7)

To a stirring solution of 6 (1.0 g, 2.69 mmol) in CH$_2$Cl$_2$ (20 mL) at 0° C. was added BBr$_3$ (1.12 mL, 13.44 mmol). The reaction mixture was allowed to warm up to room temperature and was allowed to stir for 1 hour. At this time, the reaction was quenched with the addition of water (10 mL). Solid will precipitate from the mixture, which was obtained via filtration and was purified via chromatography (30%→70%→100% Ethyl Acetate:Hexanes) to obtain 400 mg of the final product 7.

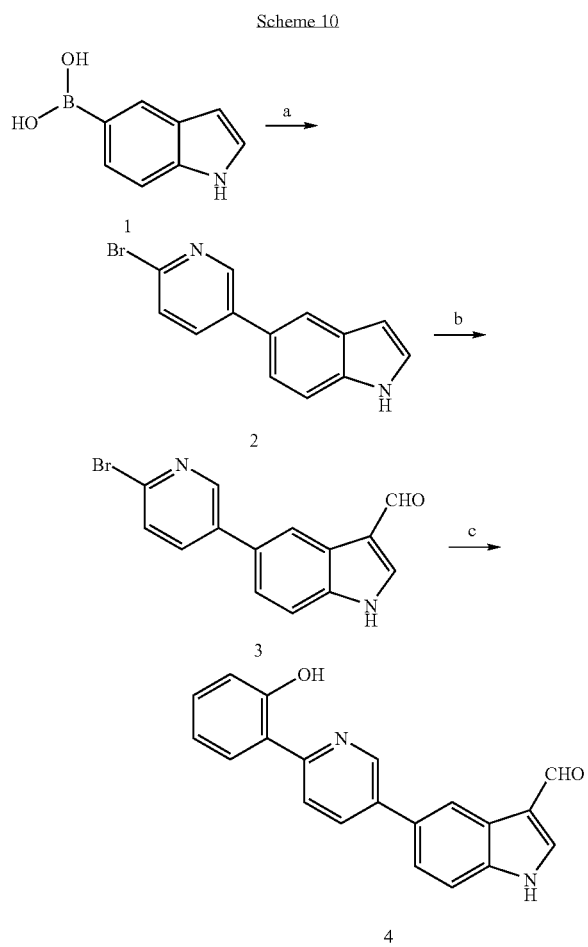

a. 6-Bromo-3-iodopyridine, Pd tetrakis, cesium carbonate, DME: H₂O; b. DMF, POCl₃; c. 2-Hydroxy benzeneboronic acid, Pd tetrakis, cesium carbonate, DME: H₂O

5-(4-Bromopyridin-3-yl)-1H-indole (2)

To a solution of 1 (3.093 g, 10.93 mmol) in 30 mL of dimethoxyethane:toluene ethanol:water (10:1:3:6) was added 6-bromo-3-iodopyridine (3.10 g, 10.93 mmol), cesium carbonate (8.90 g, 27.33 mmol) and 5 mol % Pd(PPh₃)₄ under inert atmosphere. The reaction mixture was heated at 90° C. for 3 hours. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na₂SO₄), filtered and concentrated to give crude as red oil. The material was further purified via column chromatography (10%->35% EtOAc in Hexanes) to give 1.8 g of 2 as white solid.

5-(4-Bromopyridin-3-yl)-1H-indole-3-carbaldehyde (3)

In a 100-ml round-bottom flask is placed 2.8 mL of dimethylformamide (2.74 g, 3.74 mmol). The flask and the content was cooled in an ice-salt bath for about 0.5 hour and 0.86 mL (1.44 g, 94 mmol) of freshly distilled phosphorusoxychloride is subsequently added with stirring to the dimethylformamide dropwise. Then a solution of 2 (1.00 g, 3.66 mmol) in 1 mL of dimethylformamide is added to the above solution slowly. After the addition, the temperature of the solution is brought to 40° C. and allowed to stir for an hour. At this time, 1N NaOH (10 mL) was added to the reaction mixture dropwise. The resulting mixture is heated rapidly to the boiling point and allowed to cool to room temperature. The resulting precipitate is collected on a filter and the solid was further washed with water. Compound 3 obtained from this procedure was pure enough for the next reaction.

5-(6-(2-Hydroxyphenyl)pyridin-3-yl)-1H-indole-3-carbaldehyde (4)

The title compound was prepared in analogous manner as described for 2. Thus, starting from 3 (0.1 g, 0.33 mmol) and 2-hydroxy benzeneboronic acid instead of 6-bromo-3-iodopyridineboronic acid following the above described procedure gave 50 mg of pure 4.

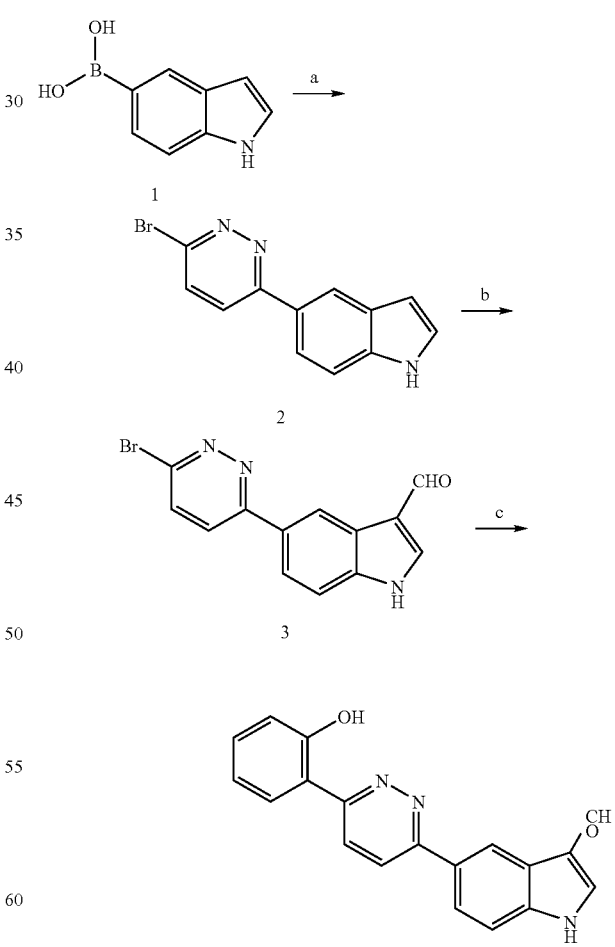

a. 3,6-dichloropyridazine, Pd tetrakis, cesium carbonate, DME: H₂O; b. DMF, POCl₃; c. 2-Hydroxy benzeneboronic acid, Pd tetrakis, cesium carbonate, DME: H₂O

5-(6-Bromopyridazin-3-yl)-1H-indole (2)

To a solution of 1 (3.093 g, 10.93 mmol) in 30 mL of dimethoxyethane:toluene:ethanol:water (10:1:3:6) was added 3,6-dichloropyridazine (1.63 g, 10.93 mmol), cesium carbonate (8.90 g, 27.33 mmol) and 5 mol % Pd(PPh$_3$)$_4$ under inert atmosphere. The reaction mixture was heated at 90° C. for 3 hours. After completion, reaction mixture was cooled to room temperature and was concentrated in vacuo. The residue was taken up in 10 mL water and the aqueous layer was washed with ethylacetate (2×25 mL). The organic layers were collected, washed with brine (2×15 mL), dried (Na$_2$SO$_4$), filtered and concentrated to give crude as red oil. The material was further purified via column chromatography (10%->35% EtOAc in Hexanes) to give 1.8 g of 2 as white solid.

5-(4-Bromopyridazin-3-yl)-1H-indole-3-carbaldehyde (3)

In a 100-ml round-bottom flask is placed 2.8 mL of dimethylformamide (2.74 g, 3.74 mmol). The flask and the content was cooled in an ice-salt bath for about 0.5 hour and 0.86 mL (1.44 g, 94 mmol) of freshly distilled phosphorusoxychloride is subsequently added with stirring to the dimethylformamide dropwise. Then a solution of 2 (1.00 g, 3.65 mmol) in 1 mL of dimethylformamide is added to the above solution slowly. After the addition, the temperature of the solution is brought to 40° C. and allowed to stir for an hour. At this time, 1N NaOH (10 mL) was added to the reaction mixture dropwise. The resulting mixture is heated rapidly to the boiling point and allowed to cool to room temperature. The resulting precipitate is collected on a filter and the solid was further washed with water. Compound 3 obtained from this procedure was pure enough for the next reaction.

5-(6-(2-Hydroxyphenyl)pyridazin-3-yl)-1H-indole-3-carbaldehyde (4)

The title compound was prepared in analogous manner as described for 2. Thus, starting from 3 (0.1 g, 0.33 mmol) and 2-hydroxy benzeneboronic acid instead of 6-bromo-3-iodopyridineboronic acid following the above described procedure gave 50 mg of pure 4.

Compounds of the invention may be prepared by any process known to be applicable to the preparation of chemically-related compounds. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

Biological Assays:

As stated hereinbefore the derivatives defined in the present invention possess anti-proliferation activity. These properties may be assessed, for example, using one or more of the procedures set out below:

In Vitro Assay of AMPK Activity:

AMPK activity was measured by the phosphorylation of the amino-teminal fragment of human acetyl CoA carboxylase-type 1, amino acids 1-120. The fragment was expressed as a biotinylated fusion protein in *E. coli*. The enzyme assay was conducted in a 5 ul reaction mixture containing 60 mM HEPES, pH7.0, 50 mM NaCL, 1 mM DTT, 5 mM MgCL2, 0.05% Tween-20, 100 uM ATP and with 25 uM AMP as a positive control. The reaction was carried out at room temperature for 60 minutes and stopped by addition of 5 ul of stop solution consisting of 20 mM EDTA, 0.1% BSA, 1% Triton-X-100, 0.01% Tween-20, 100 mM Tris pH8.0, 1:5,000 dilution of internally producted anti-pS79 (acetyl CoA carboxylase-1) purified rabbit polyclonal antibody, 40 ug/ml of AlphaScreen (Perkin Elmer) Acceptor beads and 40 ug/ml of AlphaScreen (Perkin Elmer) donor beads. The reaction mixture was further incubated at RT for 2 hours and analyzed on Fusion-Alpha microplate analyzer.

Western Blot Analysis of AMPK Activity In Vitro:

The AMPK assay was performed in a 25 ul reaction volume with the same reaction buffer as AMPK alpha assay at 30 C for 30 minutes. The reaction was stopped with SDS-PAGE sample buffer. The phosphorylated-GST-ACC was subjected to western blot analysis with anti-phospho-serine 79-ACC1 antibody (Cell Signaling Technologies). AMPK used in the assays described above was partially purified (Blazquez, C. et. al.).

The AMP-activated protein kinase is involved in the regulation of ketone body production by astrocytes. J. Neurochem. 73: 1674 (1999)) from HEKs (a human embryonic kidney cell line) and unless otherwise specified, chemicals used in the above assay were supplied by Sigma.

The following TABLE B lists compounds representative of the invention and their activity in an in vitro AMPK assay. In this assay, the following grading was used: I≧50 μM, 50 μM>II>10 μM, and III≦10 μM for ED$_{50}$.

TABLE B

| Compound No. | ED50 |
|---|---|
| 1 | II |
| 2 | III |
| 3 | III |
| 4 | II |
| 5 | III |
| 6 | I |
| 7 | III |
| 8 | III |
| 9 | II |

The patent and scientific literature referred to herein establishes the knowledge that is available to those with skill in the art. All U.S. patents and published or unpublished U.S. patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula I:

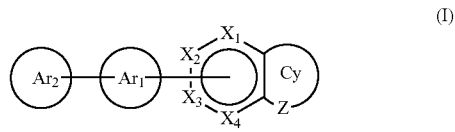

or a salt thereof, wherein

X₁, X₃ and X₄ are independently selected from the group consisting of CR₁, and N, where each R₁ is independently hydrogen, an electron-withdrawing group or an electron releasing group;

X₂ is C;

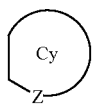

is a substituted or unsubstituted 5- or 6-membered heteroaryl; where Z is O, N or NH;

is an aryl or substituted aryl group and is connected to X₃; and

is substituted phenyl, wherein at least two substituents are hydroxyl.

2. A compound having the formula:

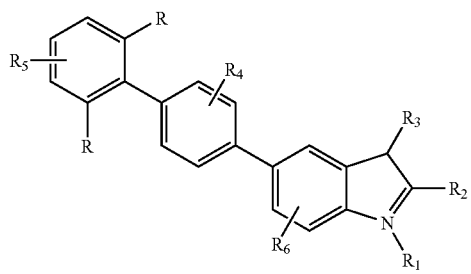

or a salt thereof, wherein $R_1$, $R_2$, $R_4$, $R_5$ and $R_6$ are independently hydrogen or one or more electron releasing groups, $R_3$ is hydrogen, CN, —CHNOH, —CONH₂ or —CHO and each R is selected from H or hydroxyl, wherein at least one R is hydroxyl.

3. The compound of claim 1 or a salt thereof wherein each $R_1$ is independently hydrogen or an electron withdrawing group.

4. The compound of claim 1 or a salt thereof wherein Ar₂ is 2,6-dihydroxyphenyl.

5. The compound of claim 1 or a salt thereof, wherein each $R_1$ is independently selected from the group consisting of hydrogen, hydroxy, halogen, substituted or unsubstituted amino, substituted or unsubstituted alkoxy, substituted or unsubstituted alkylthio CF₃, CN, NO₂, N₃, substituted or unsubstituted alkylsulfonyl, acyl, aliphatic, substituted aliphatic, aryl, and heterocyclic.

6. The compound of claim 5 or a salt thereof, wherein Ar₂ is 2,6-dihydroxyphenyl.

7. The compound according to claim 1 represented by formula (III):

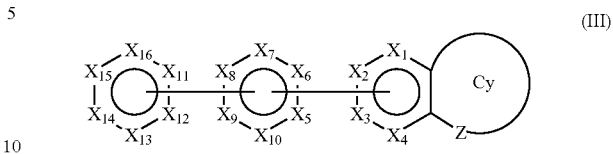

or a, salt thereof, wherein at least two of $X_{11}$-$X_{16}$ is C-OH and the remainder of $X_5$-$X_{16}$ are independently selected from the group consisting of C and CR₁, where R₁ is independently selected from the group consisting of hydrogen, hydroxy, halogen, substituted or unsubstituted amino, substituted or unsubstituted alkoxy, substituted or unsubstituted alkylthio, CF₃, CN, NO₂, N₃ substituted or unsubstituted alkylsulfonyl, acyl, aliphatic, substituted aliphatic, aryl, heteroaryl, and heterocyclic; and

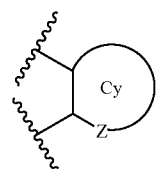

is selected from the group consisting of

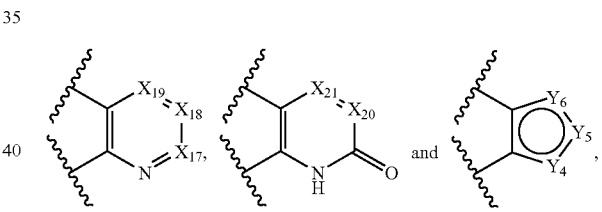

where $X_{17}$-$X_{21}$ are independently selected from the group consisting of C, CR₁ or N, where R₁ is independently selected from the group consisting of hydrogen, hydroxy, halogen, substituted or unsubstituted amino, substituted or unsubstituted alkoxy, substituted unsubstituted alkythio, CF₃, CN, NO₂, N₃, CHNOH, CONH₂, CHO, substituted or unsubstituted alkylsulfonyl, acyl, aliphatic, substituted aliphatic, aryl, heteroaryl, and heterocyclic; Y₄ is O, N or NH; Y₅ and Y₆ are independently selected from the group consisting of C, CR₁, O, S, N and NH; and $X_1$-$X_4$ are as set forth in claim 1.

8. The compound according to claim 1 represented by formula (IV):

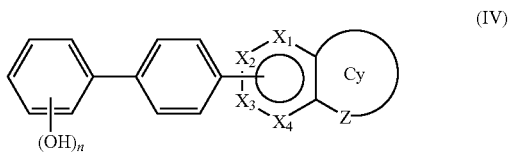

or a salt thereof, wherein

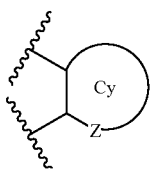

is selected from the group consisting of

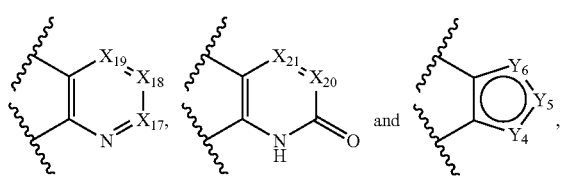

where $X_{17}$-$X_{21}$ are independently selected from the group consisting of C, $CR_1$ and N, where $R_1$ is independently selected from the group consisting of hydrogen, hydroxy, halogen, substituted or unsubstituted amino, substituted or unsubstituted alkoxy, substituted or unsubstituted alkylthio, $CF_3$, CN, $NO_2$, $N_3$, CHNOH, $CONH_2$, CHO, substituted or unsubstituted alkylsulfonyl, acyl, aliphatic, substituted aliphatic, aryl, heteroaryl, and heterocyclic; $Y_4$ is O, N or NH; $Y_5$-$Y_6$ are independently selected from the group consisting of C, $CR_1$, O, S, N or NH; n is 2 or 3; and $X_1$-$X_4$ have the meaning set forth in claim 1.

9. A compound selected from the compounds delineated in the table below and salts thereof:

TABLE A

| Compound # | Structure |
|---|---|
| 1 | |
| 2 | |
| 3 | 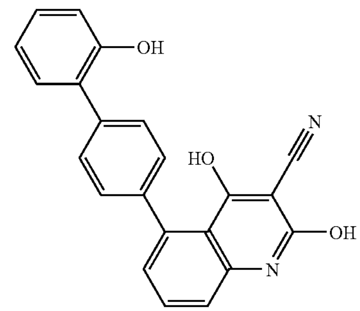 |
| 4 | 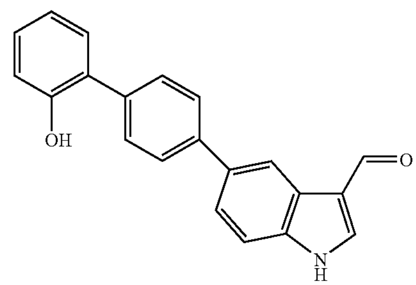 |
| 5 | 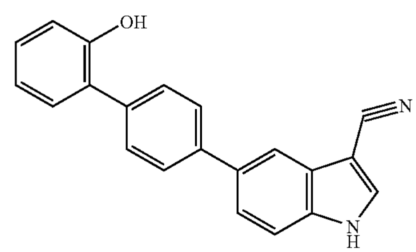 |
| 6 | 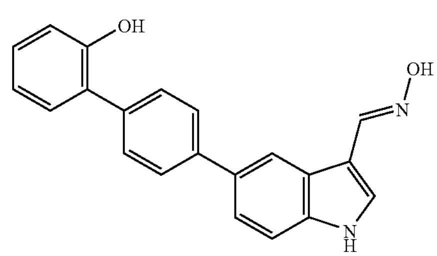 |
| 8 | 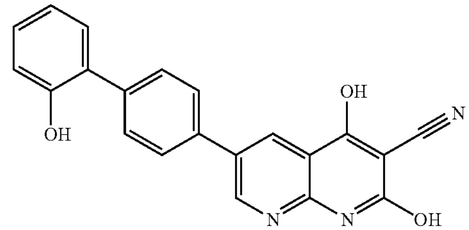 |

TABLE A-continued

| Compound # | Structure |
|---|---|
| 10 | (structure) |
| 11 | (structure) |

10. A compound selected from 5-(2,6-Dihydroxybiphenyl)-1H-indole-3-carbonitrile, 5-(2,6-Dihydroxybiphenyl)-1H-indole-3-carboxamide, 5-(6-(2-Hydroxyphenyl)pyridin-3-yl)-1H-indole-3-carbaldehyde, and 5-(6-(2-Hydroxyphenyl)pyridazin-3-yl)-1H-indole-3-carbaldehyde and salts thereof.

11. A pharmaceutical composition comprising a therapeutically effective amount of a compound of claim 1 and salts thereof, in combination with a pharmaceutically suitable carrier.

12. A compound selected from the compounds delineated in the table below and salts thereof:

| Compound # | Structure |
|---|---|
| 12 | (structure) |
| 13 | (structure) |
| 14 | (structure) |
| 15 | (structure) |
| 16 | (structure) |
| 17 | (structure) |
| 19 | (structure) |

-continued
| Compound # | Structure |
|---|---|
| 21 | 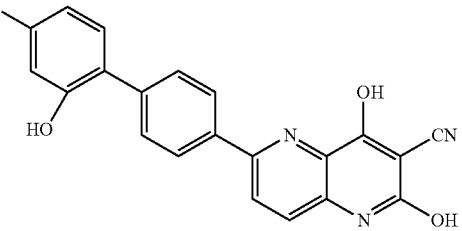 |
-continued
| Compound # | Structure |
|---|---|
| 22 | 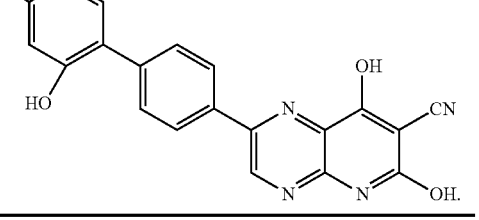 |
* * * * *

UNITED STATES PATENT AND TRADEMARK OFFICE
CERTIFICATE OF CORRECTION

PATENT NO.        : 8,273,744 B2
APPLICATION NO.   : 12/365671
DATED             : September 25, 2012
INVENTOR(S)       : Neal Birnberg et al.

It is certified that error appears in the above-identified patent and that said Letters Patent is hereby corrected as shown below:

At Column 45
   In claim 1, at line 24, delete "X3" and insert -- X2 --; and
   In claim 5, at line 65, after "aryl," insert -- heteroaryl --.

At Column 46
   In claim 7, at line 12, after "is" delete "C-OII" and insert -- C-OH --; and
   In claim 7, at line 49, after "alkoxy, substituted" add -- or --.

At Column 49
   In claim 11, at line 36, after "claim 1" delete "and salts" and insert -- or a salt --.

Signed and Sealed this
Eighth Day of January, 2013

David J. Kappos
*Director of the United States Patent and Trademark Office*